US006767335B1

(12) United States Patent
Helg

(10) Patent No.: US 6,767,335 B1
(45) Date of Patent: Jul. 27, 2004

(54) SYRINGE OF SINGLE-USE TYPE INTENDED FOR INJECTION OR LAB TESTS

(75) Inventor: Rolf Helg, Stockholm (SE)

(73) Assignee: HelgMediTech AB, Saltsjobaden (SE)

( * ) Notice: Subject to any disclaimer, the term of this patent is extended or adjusted under 35 U.S.C. 154(b) by 251 days.

(21) Appl. No.: 10/129,868

(22) PCT Filed: Nov. 24, 2000

(86) PCT No.: PCT/SE00/02335
§ 371 (c)(1),
(2), (4) Date: May 15, 2002

(87) PCT Pub. No.: WO01/41842
PCT Pub. Date: Jun. 14, 2001

(30) Foreign Application Priority Data

Nov. 26, 1999 (SE) .............................. 9904311

(51) Int. Cl.[7] .............................................. A61M 5/00
(52) U.S. Cl. ...................... 604/110; 604/195; 604/218; 604/220; 604/240
(58) Field of Search ................................ 604/100, 187, 604/194, 195, 225, 218, 220, 240, 243

(56) References Cited

U.S. PATENT DOCUMENTS

| 4,955,869 | A | | 9/1990 | Bin |
| 5,064,419 | A | | 11/1991 | Gaarde |
| 5,242,402 | A | * | 9/1993 | Chen ........................... 604/110 |
| 5,496,278 | A | | 3/1996 | Buff |
| 5,531,694 | A | * | 7/1996 | Clemens et al. ............. 604/110 |
| 5,533,975 | A | | 7/1996 | Lu |
| 5,562,627 | A | | 10/1996 | Chen |
| 6,050,974 | A | * | 4/2000 | Allard et al. ................ 604/110 |
| 6,074,370 | A | * | 6/2000 | Pressly et al. ............... 604/195 |
| 6,117,107 | A | * | 9/2000 | Chen ........................... 604/110 |
| 6,179,812 | B1 | * | 1/2001 | Botich et al. ................ 604/110 |
| 6,206,857 | B1 | * | 3/2001 | Chen ........................... 604/195 |

FOREIGN PATENT DOCUMENTS

EP 0 413 414 A 2/1991

* cited by examiner

Primary Examiner—Brian L. Casler
Assistant Examiner—Jeremy Thissell
(74) Attorney, Agent, or Firm—Frishauf, Holtz, Goodman & Chick, P.C.

(57) ABSTRACT

The invention refers to a syringe of single-use type intended for injection or lab tests with an injection needle slidable into the syringe after usage. The intention with this is to eliminate the risk for prick injuries when the syringe is handled after usage. A design of a single-use syringe such that the needle becomes kept in the interior of the syringe after usage has proved to be involved by different kinds of complications and has made the syringe complicated and expensive to manufacture. An uncomplicated and reliable syringe of the kind stated in the introduction is achieved according to the invention by the fact that the plunger (2) of the syringe is provided with a coupling device (12) designed such that in the completely pushed in position of the plunger the rear part of the injection needle (6) is coupled to the plunger (2) and follows the plunger when the plunger is withdrawn. Moreover, the coupling device is provided with a canal (13) penetrating the plunger to the rear side of the plunger, and is designed such that when the point of the injection needle is pressed against the cover base (4) of the syringe by the plunger being pushed, the needle slides through said canal in the plunger until only the point portion of the needle is situated in the plunger, where the point portion is fastened.

36 Claims, 3 Drawing Sheets

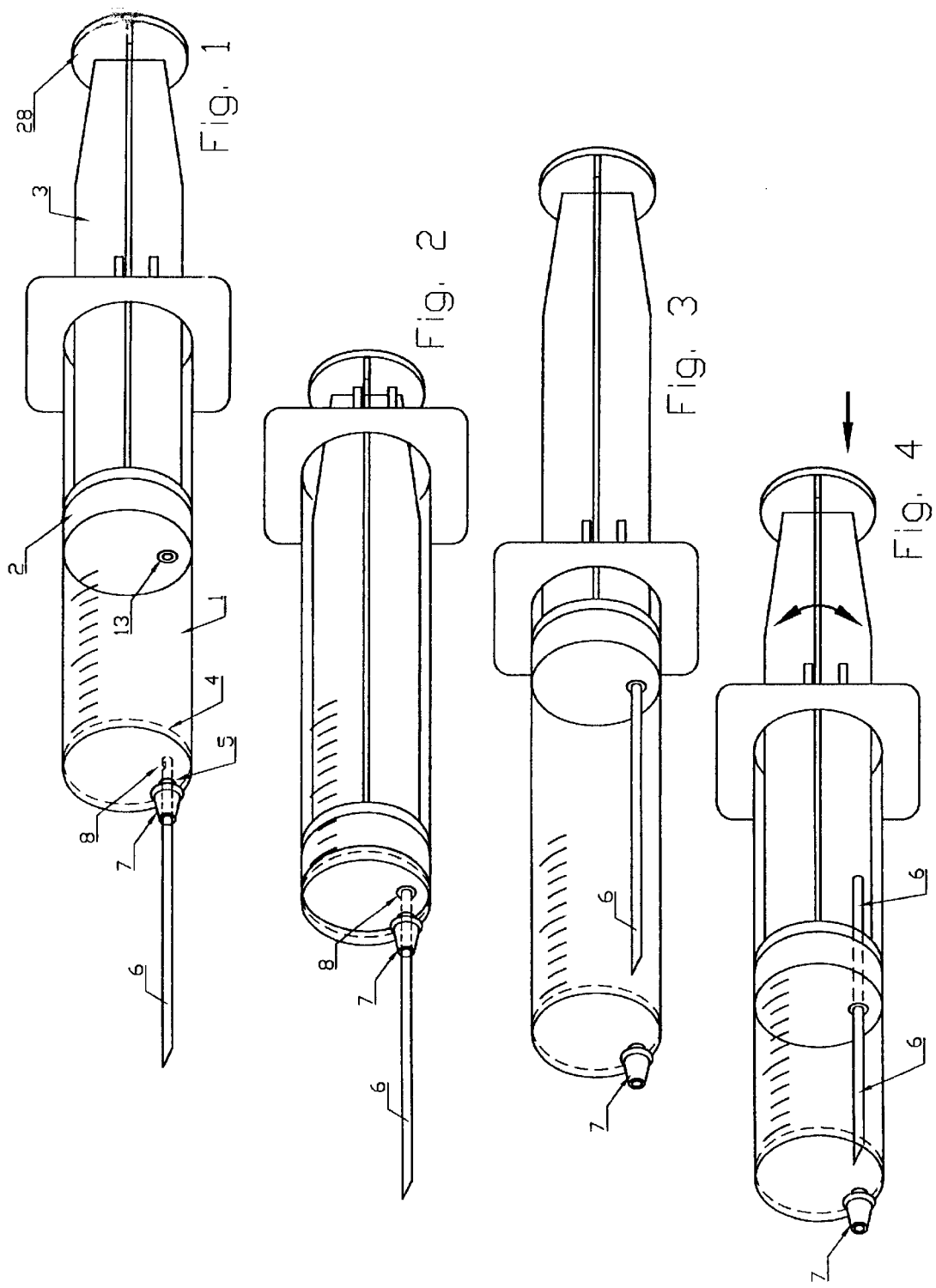

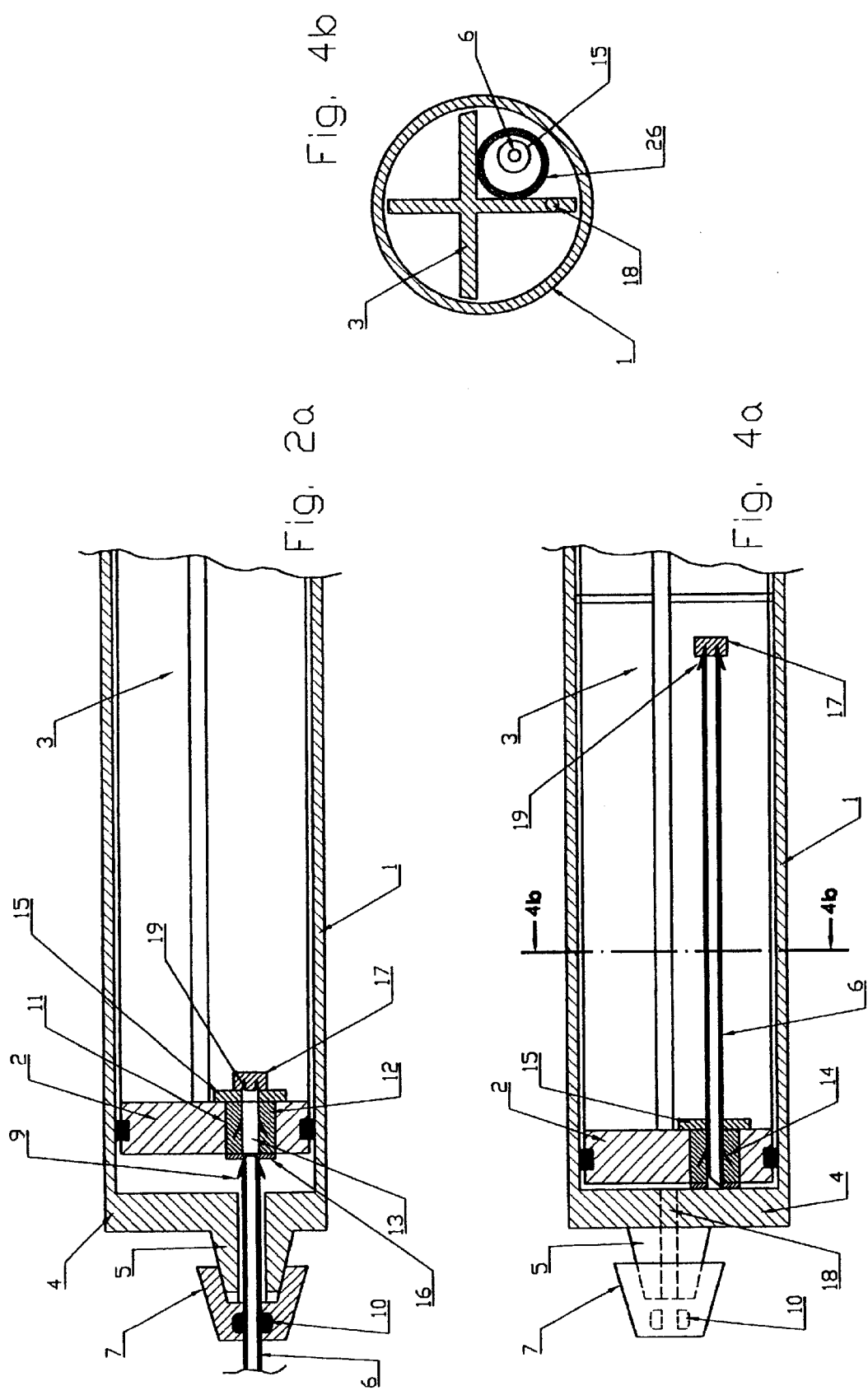

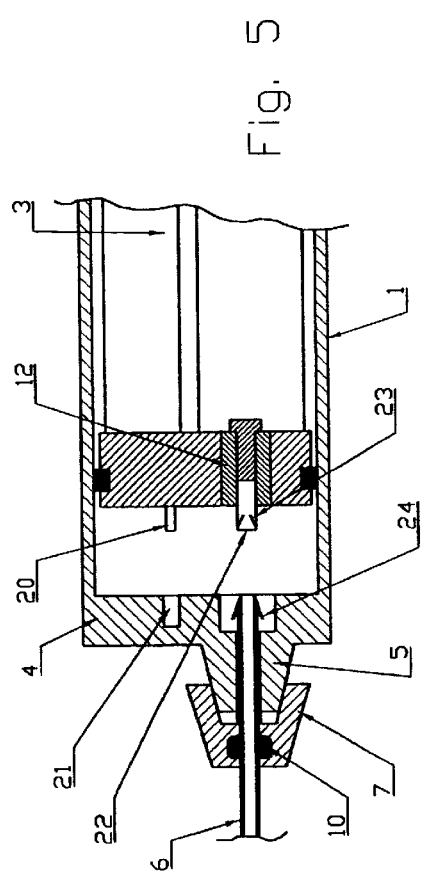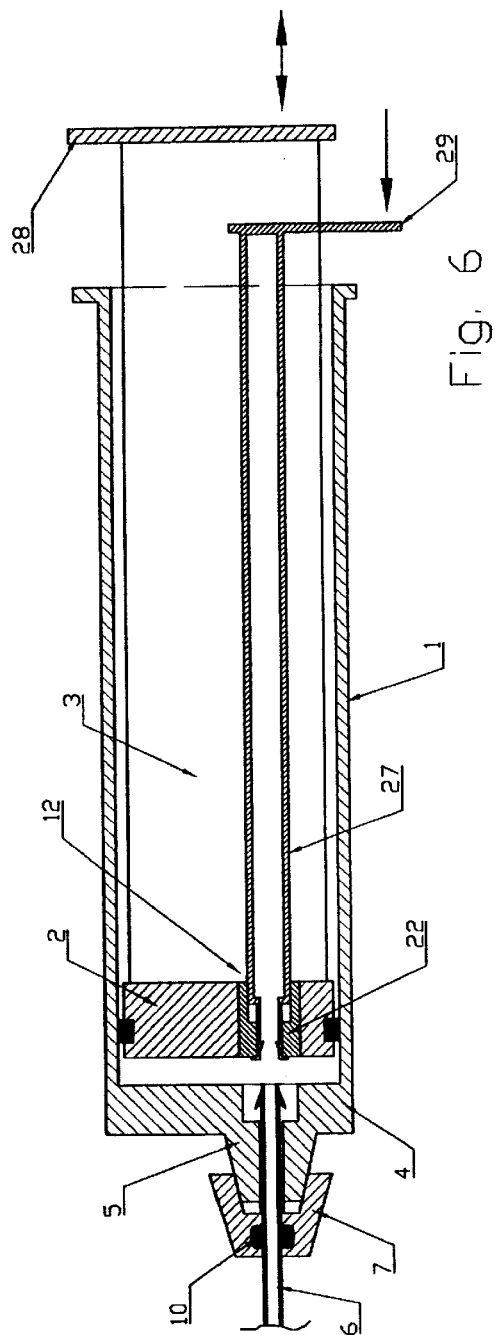

SYRINGE OF SINGLE-USE TYPE INTENDED FOR INJECTION OR LAB TESTS

This application is the United States national phase application of International Application No. PCT/SE00/02335 filed Nov. 24, 2000 (published in English).

BACKGROUND OF THE INVENTION

This invention deals with a syringe of single-use type intended for injection or lab tests of the kind given in the introduction part of the following patent claim 1.

Currently used syringes for injection are normally of single-use type and of simple design. They are mass-produced of plastic material consisting of a cover, inside which there is a movable plunger constructed in one piece with a protrusion forming a plunger pole. The plunger is equipped with a simple ring-shaped packing, and at the bottom of the cover there is a gripper for attaching a mountable injection needle which extends through the base of the cover. Before usage, a detachable needle protection cover, on the needle, protects the needle.

After usage, the syringe is usually thrown away into a special container for risk waste. Sometimes this is forgotten and the syringe may by mistake be used several times, which means considerable risks for patients.

Another disadvantage about conventional single-use syringes involves accidental risk for personnel by the fact they may easily get stung when handling it. Normally, as mentioned, the syringe needle is protected by a needle protection cover before usage. This should be re-applied onto the needle after usage, before throwing away the syringe. The opening of the needle protection cover is of small diameter, although to some extent conical shaped, and it may be hard to move the needle into the opening, safely. If you miss some time, there is a considerable risk of pricking your finger, and this risk is imminent when working in situations when there is little time and stress. The frequency of incidents for personnel who often handle syringes of this kind, is as high as 80%, according to an investigation counting the number of incidents when people prick their fingers, occurring at least once per person. Even already used, loose injection needles imply risks, even when contained in risk waste containers, since it happens that needles penetrate container walls.

To avoid or prevent these potential incidents, it is known to have a coupling device applied to the plunger part facing the cover base, by which the plunger when maximally pushed in may be connected to the inner end of the needle, after which the needle may be retracted into the space between the cover base and the plunger, by maximally pulling it out. In this position, however, the syringe may not be thrown away, since there is a risk that the maximally protruding plunger pole may be somewhat pushed in, thus making the needle protrude from the cover base.

There is, however, the possibility of turning the plunger pole and thereby the plunger, to some extent, so that the needle is displaced sideways a bit, and thereafter break the plunger pole. A disadvantage then is that the plunger by bending tensions may become tilted or the syringe cover breaks, so that remaining liquid in the syringe may leak out.

Another well-known solution as regards the protruding plunger pole consists in after having turned the plunger pole somewhat, slightly reminiscent of above-mentioned turning, the whole plunger is pushed back, whereby the needle end hits the cover base, and the needle is strongly bent backwards. A certain amount of force is required for this, and in unfortunate cases it may happen that the needle end penetrates the base, whereby there is considerable risk of the needle penetrating into the hand that holds the cover base of the syringe.

Yet another known solution to the problem of encasing the injection needle after usage inside the syringe, consists in applying, according to EP 0413414, a mechanism in the cover base, which upon the pressure of the plunger on the cover base pushes in a cap exposing a hole through the plunger ending in a space behind the plunger, simultaneously releasing the needle attachment device in the cover base, permitting a spring mechanism to throw the needle backwards in the syringe into aforementioned space behind the plunger front end, which is a cavity inside the plunger pole. This is an expensive and complicated syringe, which furthermore has the disadvantage that the needle has to be assembled upon manufacturing the syringe and cannot be replaced, if needed, afterwards, in which case the whole syringe must be replaced

SUMMARY OF THE INVENTION

The object of the present invention is to achieve a single-use syringe of afore-mentioned kind, which combines simplicity with higher security for avoiding accidents when handling the syringes, compared to known syringes.

This has, according to the invention, been achieved by giving the syringe the characteristics that are indicated in patent claim 1. Instead of making the needle bent, which is the case in one of the known solutions, will the solution according to the invention, after having pushed in the plunger a second time after having dragged in the needle into the space between the cover base and the plunger, involve the pushing of the needle through a hole penetrating the plunger until the needle point is positioned closely level with the front face of the plunger with the rest of the needle in the plunger and a space behind it. For this push-in of the plunger, less force is required compared to the known solution whereby the needle was bent and shortened, and this means that the risk of pushing the needle through the cover base is negligible. Preferably, the needle point part be safely held fast in the front end of the plunger by equipping the penetrating hole in the plunger with a surrounding, embracing, elastic device as indicated in claim 2.

Other preferred embodiments of the syringe according to the invention are stated in the sub-claims and the folloeing description.

BRIEF DESCRIPTION OF THE DRAWINGS

The invention is specified more in detail in the following with reference to the attached drawings, schematically showing different embodiments of syringes according to the invention, and on which FIGS. 1–4 are perspective views of a single-use syringe of simplest kind, showing four different positions of the plunger under which the injection needle is brought inside the syringe; FIG. 2a is a longitudinal section of the syringe showing the cover base and coupling device in the position shown by FIG. 2, FIGS. 4a and 4b are a longitudinal section and a cross-section along the line IVb—IVb in FIG. 4a of the syringe cover base with coupling device in the position shown in FIG. 4, but with the plunger pushed in and stopped by the cover base, FIG. 5 is a longitudinal section of the cover base of a modified syringe, and FIG. 6 is a longitudinal section of a preferred embodiment.

DETAILED DESCRIPTION

FIGS. 1–4 show a common type of syringe of single-use type, which has been modified in accordance with the Invention. The syringe has a cover 1 of transparent plastic, in which a plunger 2 equipped with a plunger pole 3 is slidably mounted. On the exterior part of the cover base, there is in customary fashion a slightly conical, protruding attachment device 5 for an injection needle 6 with the needle fixed in a hollow gripper 7 of the same interior conicity as the attachment device, exteriorly.

For adapting this known syringe in accordance with the invention, the rear part 8 of the needle is prolonged and extends through the cover base and a little further into the interior of the syringe. The needle is furthermore applied in a slidable fashion with large friction in the gripper 7. The rear part 6 of the needle is furthermore equipped with a number of forward directed exterior, springy barbs 9, as shown in FIG. 2a. In the gripper 7, the needle is surrounded by a springy rubber packing 10, creating sufficient friction to keep the needle in place for normal usage of the syringe, such as injection. According to the invention, the plunger 2 has a penetrating hole 11, into which a coupling device 12 of elastic material is slidably inserted. The coupling device 12 is equipped with a penetrating canal 13, into which the rear part 8 of the needle 6 may slide in during the movement of the plunger up to the cover base 4. The barbs 9 of the needle are pressed into the elastic material in the canal 13 wall, and in this wall, cuts 14 may be done to improve the grip of the barbs 9. The coupling device 12 is designed as a thick-wall sleeve with a flange 15, resting on the rear face of the plunger 2. Furthermore, there is a thin piece of packing 16 covering the front aperture of the canal 13 and a plug 17 covering the rear aperture of said canal 13, detachably attached on the flange 15.

FIG. 2a shows the syringe with the plunger 13 almost maximally pushed in to make the syringe ready for lab tests or finishing an injection. Alternatively, the figure shows the position of the plunger, when the syringe has been emptied as much as possible after a sample test. Thereafter, the task is to remove the needle 6 swiftly and simply. This is done by pushing in the plunger somewhat further. The packing piece 16 is penetrated by the rear end of the needle 6 which slides into the canal 13 as some liquid in the syringe is squeezed out through the needle via a space between the needle and the wall of the canal 13, until the barbs 9 are pressed into the wall of canal 13 or into the cuts 14. Thereafter the plunger 2 is pulled out totally, whereby the needle 6 is transported to a position indicated in FIG. 3 with the point of the needle in front of the interior wall of the cover base. The elastic packing 10 bounces inwards and covers the aperture of gripper 7 after the passage of the needle 6. Thereafter the plunger 2 is turned somewhat, as shown in FIGS. 4a and 4b, and pushed in again all the way down until the front end of the needle 6 rests on the interior bottom wall positioned somewhat away from the hole 18. Thereby, the needle is pushed through the canal 13 of the plunger 2, whereby the plug 17, which preferably has a ring-shaped cut 19 of the same diameter as the rear end of the needle, is pressed onto the needle end as a sealing plug transported along with the needle to the position shown in FIG. 4a, in which position the needle 6 has its front end clutched in the canal 13 of the plunger 2.

Remaining liquid in the syringe will thereby be prevented from leaking out from the ring-shaped packing 10 and the sealing plug 17.

It may be hard to avoid non-intended coupling of needle end and coupling device 12. To prevent such a coupling, the syringe may be designed as shown in FIG. 5, with a protruding peg 20 on the front of the plunger and corresponding hole 21 in the bottom wall of the syringe positioned so that the coupling device 12 will be centred on the hole 18 for the needle, when the peg is centred on the hole 21. The plunger 3 may then be pushed all the way down, when coupling takes place. Here the coupling shown depicts the action when the coupling device 12, on which there is a protruding tube 22 with interior barbs 23 arranged so as to clutch a ring-shaped protrusion 24 on the outside of the rear part 8 of the needle, which resides in a slightly wider ring-shaped socket 25. At other turning positions of the plunger 2, the non-intended coupling is prevented by the peg 20 hitting the bottom wall of the syringe to the side of the hole 25. Alternatively, the peg 20 may of course be positioned on the bottom wall, and a hole 21 in the front-end of the plunger 2.

To prevent the needle from becoming reachable in the position shown in FIG. 4a, the plunger 3 may be equipped with a tube 26, closed at its rear end, and embracing the needle, as shown in FIG. 4b.

The remaining liquid in the syringe may be seen as an inconvenience. However, the space for this, may be lowered almost to zero in the embodiment according to FIG. 6. This embodiment is in principle the same as in FIG. 5, as regards the coupling function, but the coupling device 12 with the tube 22 are equipped with a tube-shaped pressure device 27, and the tube 22 is normally positioned in the plane of the front face of the plunger 2. The plunger 2 may thus be pushed all the way down by the plunger pole without causing coupling. Coupling can only take place on purpose by, in this position, pushing in the pressure device 27, in such a way that the tube 22 is pushed out around the rear end of the needle 6. For operating the plunger pole 3 and the pressure device 27, they should preferably be provided with a handle 28 and a pressure plate 29, respectively. When coupling has been accomplished, the plunger 2 should be retracted to a rearmost position, where a slight turning of the plunger should take place followed by pushing the plunger back all the way down so that the needle is pushed into the tube-shaped pressure device 27 with the sharp end of the needle clutched by the elastic material in the coupling device 12.

The invention is of course not limited to the examplifying embodiments shown and described here, but may be modified in numerous ways within the scope of the invention as defined by the patent claims.

What is claimed is:

1. A syringe of single-use type intended for injection or lab tests with an injection needle (6) slidable into the syringe after usage, comprising a tube-shaped cover (1) with a cover base (4), a hole (18) in the cover base through which an inner end (8) of the needle extends, an attachment device (5) applied on an exterior part of the cover base, onto which a gripper (7) embracing the injection needle slidably with large friction has been detachably assembled, and a displaceable plunger (2) inside the cover (1) movable by a plunger pole (3), said plunger (2) equipped with a coupling device (12) interacting with the inner end of the needle, for coupling of these when the plunger is maximally pushed in, resting on the cover base, characterised in that a coupling device (12) of the plunger is sealingly inserted in a through-hole (11) in the plunger such that by pulling out the plunger, after coupling with the injection needle, the needle is retractable into the cover (1) between the cover base (4) and the plunger (2) and by pressing the needle end against the interior wall of the cover base is pushable into a space behind the plunger front-end (2) upon movement of the plunger onto the cover base (4).

2. Single-use syringe according to claim 1, characterised in that the front end of the needle after having pushed the needle into the space behind the plunger front-end (2) is held fast by an elastic embracing means (12), embracing said needle end, in the hole (11) penetrating the plunger (2) front-end.

3. Single-use syringe according to claim 2, characterised in that said space behind the plunger is the interior of cover (a), and that the rear part of the cover is sealed by a gable wall provided with an opening for the plunger pole.

4. Single-use syringe according to claim 3, characterised in that the coupling device (12) of the plunger is separately maneuverable by aid of a pressure device (27), intended for use, when the plunger is maximally pushed in, by exerting pressure on it in order to make the coupling device connection to the injection needle.

5. Single-use syringe according to claim 4, characterised in that the plunger coupling device (12) and the inner end (8) of the needle are shaped as two telescopically slidable parts with locking means (23, 24).

6. Single-use syringe according to claim 3, characterised in that the attachment device (5) for the needle gripper (7) is disposed close to the periphery of the cover base, and that a stop peg (20) is mounted between the interior of the cover base (4) and the front face of the plunger (2) preventing the plunger from being pushed in to that position at which coupling between the coupling device and the injection needle is meant to take place, and that a socket (21) is arranged in the cover base or front face of the plunger for receiving said peg (20) after aligning these by a rotation of the plunger and pushing in the plunger to position causing connection.

7. Single-use syringe according to claim 6, characterised in that the plunger coupling device (12) and the inner end (8) of the needle are shaped as two telescopically slidable parts with locking means (23, 24).

8. Single-use syringe according to claim 3, characterised in that the plunger coupling device (12) and the inner end (8) of the needle are shaped as two telescopically slidable parts with locking means (23, 24).

9. Single-use syringe according to claim 2, characterised in that said space behind the plunger front-end (2) consists in a cavity in the plunger pole, or a with said plunger pole connected part (26).

10. Single-use syringe according to claim 9, characterised in that the coupling device (12) of the plunger is separately maneuverable by aid of a pressure device (27), intended for use, when the plunger is maximally pushed in, by exerting pressure on it in order to make the coupling device connection to the injection needle.

11. Single-use syringe according to claim 10, characterised in that the plunger coupling device (12) and the inner end (8) of the needle are shaped as two telescopically slidable parts with locking means (23, 24).

12. Single-use syringe according to claim 9, characterised in that the attachment device (5) for the needle gripper (7) is disposed close to the periphery of the cover base, and that a stop peg (20) is mounted between the interior of the cover base (4) and the front face of the plunger (2) preventing the plunger from being pushed in to that position at which coupling between the coupling device and the injection needle is meant to take place, and that a socket (21) is arranged in the cover base or front face of the plunger for receiving said peg (20) after aligning these by a rotation of the plunger and pushing in the plunger to position causing connection.

13. Single-use syringe according to claim 12, characterised in that the plunger coupling device (12) and the inner end (8) of the needle are shaped as two telescopically slidable parts with locking means (23, 24).

14. Single-use syringe according to claim 9, characterised in that the plunger coupling device (12) and the inner end (8) of the needle are shaped as two telescopically slidable parts with locking means (23, 24).

15. Single-use syringe according to claim 2, characterised in that the coupling device (12) of the plunger is separately maneuverable by aid of a pressure device (27), intended for use, when the plunger is maximally pushed in, by exerting pressure on it in order to make the coupling device connection to the injection needle.

16. Single-use syringe according to claim 15, characterised in that the plunger coupling device (12) and the inner end (8) of the needle are shaped as two telescopically slidable parts with locking means (23, 24).

17. Single-use syringe according to claim 2, characterised in that the attachment device (5) for the needle gripper (7) is disposed close to the periphery of the cover base, and that a stop peg (20) is mounted between the interior of the cover base (4) and the front face of the plunger (2) preventing the plunger from being pushed in to that position at which coupling between the coupling device and the injection needle is meant to take place, and that a socket (21) is arranged in the cover base or front face of the plunger for receiving said peg (20) after aligning these by a rotation of the plunger and pushing in the plunger to position causing connection.

18. Single-use syringe according to claim 17, characterised in that the plunger coupling device (12) and the inner end (8) of the needle are shaped as two telescopically slidable parts with locking means (23, 24).

19. Single-use syringe according to claim 2, characterised in that the plunger coupling device (12) and the inner end (8) of the needle are shaped as two telescopically slidable parts with locking means (23, 24).

20. Single-use syringe according to claim 1, characterised in that said space behind the plunger is the interior of cover (a), and that the rear part of the cover is sealed by a gable wall provided with an opening for the plunger pole.

21. Single-use syringe according to claim 20, characterised in that the coupling device (12) of the plunger is separately maneuverable by aid of a pressure device (27), intended for use, when the plunger is maximally pushed in, by exerting pressure on it in order to make the coupling device connection to the injection needle.

22. Single-use syringe according to claim 21, characterised in that the plunger coupling device (12) and the inner end (8) of the needle are shaped as two telescopically slidable parts with locking means (23, 24).

23. Single-use syringe according to claim 20, characterised in that the attachment device (5) for the needle gripper (7) is disposed close to the periphery of the cover base, and that a stop peg (20) is mounted between the interior of the cover base (4) and the front face of the plunger (2) preventing the plunger from being pushed in to that position at which coupling between the coupling device and the injection needle is meant to take place, and that a socket (21) is arranged in the cover base or front face of the plunger for receiving said peg (20) after aligning these by a rotation of the plunger and pushing in the plunger to position causing connection.

24. Single-use syringe according to claim 23, characterised in that the plunger coupling device (12) and the inner end (8) of the needle are shaped as two telescopically slidable parts with locking means (23, 24).

25. Single-use syringe according to claim 20, characterised in that the plunger coupling device (12) and the inner end (8) of the needle are shaped as two telescopically slidable parts with locking means (23, 24).

26. Single-use syringe according to claim 1, characterised in that said space behind the plunger front-end (2) consists in a cavity in the plunger pole, or a with said plunger pole connected part (26).

27. Single-use syringe according to claim 26, characterised in that the coupling device (12) of the plunger is separately maneuverable by aid of a pressure device (27), intended for use, when the plunger is maximally pushed in, by exerting pressure on it in order to make the coupling device connection to the injection needle.

28. Single-use syringe according to claim 27, characterised in that the plunger coupling device (12) and the inner end (8) of the needle are shaped as two telescopically slidable parts with locking means (23, 24).

29. Single-use syringe according to claim 26, characterised in that the attachment device (5) for the needle gripper (7) is disposed close to the periphery of the cover base, and that a stop peg (20) is mounted between the interior of the cover base (4) and the front face of the plunger (2) preventing the plunger from being pushed in to that position at which coupling between the coupling device and the injection needle is meant to take place, and that a socket (21) is arranged in the cover base or front face of the plunger for receiving said peg (20) after aligning these by a rotation of the plunger and pushing in the plunger to position causing connection.

30. Single-use syringe according to claim 29, characterised in that the plunger coupling device (12) and the inner end (8) of the needle are shaped as two telescopically slidable parts with locking means (23, 24).

31. Single-use syringe according to claim 26, characterised in that the plunger coupling device (12) and the inner end (8) of the needle are shaped as two telescopically slidable parts with locking means (23, 24).

32. Single-use syringe according to claim 1, characterised in that the coupling device (12) of the plunger is separately maneuverable by aid of a pressure device (27), intended for use, when the plunger is maximally pushed in, by exerting pressure on it in order to make the coupling device connection to the injection needle.

33. Single-use syringe according to claim 32, characterised in that the plunger coupling device (12) and the inner end (8) of the needle are shaped as two telescopically slidable parts with locking means (23, 24).

34. Single-use syringe according to claim 1, characterised in that the attachment device (5) for the needle gripper (7) is disposed close to the periphery of the cover base, and that a stop peg (20) is mounted between the interior of the cover base (4) and the front face of the plunger (2) preventing the plunger from being pushed in to that position at which coupling between the coupling device and the injection needle is meant to take place, and that a socket (21) is arranged in the cover base or front face of the plunger for receiving said peg (20) after aligning these by a rotation of the plunger and pushing in the plunger to position causing connection.

35. Single-use syringe according to claim 34, characterised in that the plunger coupling device (12) and the inner end (8) of the needle are shaped as two telescopically slidable parts with locking means (23, 24).

36. Single-use syringe according to claim 1, characterised in that the plunger coupling device (12) and the inner end (8) of the needle are shaped as two telescopically slidable parts with locking means (23, 24).

\* \* \* \* \*